US011219433B2

(12) United States Patent
Stoddard et al.

(10) Patent No.: US 11,219,433 B2
(45) Date of Patent: Jan. 11, 2022

(54) INGRESS PROTECTION FOR ELECTROSURGICAL PENCIL SWITCH

(71) Applicant: COVIDIEN LP, Mansfield, MA (US)

(72) Inventors: Robert B. Stoddard, Steamboat Springs, CO (US); Ian C. McEachern, Tracy, CA (US); Michael J. Brown, Golden, CO (US)

(73) Assignee: Covidien LP, Mansfield, MA (US)

( * ) Notice: Subject to any disclaimer, the term of this patent is extended or adjusted under 35 U.S.C. 154(b) by 1039 days.

(21) Appl. No.: 14/857,893

(22) Filed: Sep. 18, 2015

(65) Prior Publication Data

US 2016/0081742 A1 Mar. 24, 2016

Related U.S. Application Data

(60) Provisional application No. 62/053,981, filed on Sep. 23, 2014, provisional application No. 62/053,992, filed on Sep. 23, 2014.

(51) Int. Cl.
*A61B 17/00* (2006.01)
*A61B 18/12* (2006.01)
(Continued)

(52) U.S. Cl.
CPC .............. *A61B 17/00* (2013.01); *A61B 18/12* (2013.01); *A61B 18/1402* (2013.01);
(Continued)

(58) Field of Classification Search
CPC . A61B 18/1402; A61B 18/1477; A61B 17/00; A61B 18/12; A61B 2018/00178; H01H 23/06
See application file for complete search history.

(56) References Cited

U.S. PATENT DOCUMENTS

D253,247 S 10/1979 Gill
4,545,375 A 10/1985 Cline
(Continued)

FOREIGN PATENT DOCUMENTS

DE 2429021 A1 1/1976
DE 2460481 A1 6/1976
(Continued)

OTHER PUBLICATIONS

Japanese Office Action dated Aug. 29, 2016, issued in JP Application No. 2015-186156.
(Continued)

*Primary Examiner* — Michael F Peffley
*Assistant Examiner* — Samantha M Good
(74) *Attorney, Agent, or Firm* — Carter, DeLuca & Farrell LLP

(57) ABSTRACT

A surgical instrument includes a switch base, a power bus coupled to the switch base, an electrical lead coupled to the power bus, an actuator operatively engaged with the power bus, an actuator operatively engaged with the power bus, a membrane, and a housing. The switch base has top, bottom, and side surfaces. The membrane is disposed over the top surface of the switch base and over the power bus to seal the top surface of the switch base. The housing defines proximal and distal ends and a switch base cavity between the proximal and distal ends. The housing includes bulkheads that form a plurality of fluid impermeable seals that are disposed adjacent one of the proximal and distal ends. The fluid impermeable seals are configured to deter fluid from penetrating a proximal portion of the switch base cavity within which the electrical lead is coupled to the power bus.

17 Claims, 3 Drawing Sheets

(51) Int. Cl.
  *A61B 18/14* (2006.01)
  *H01H 23/06* (2006.01)
  *A61B 18/00* (2006.01)
  *B29C 65/48* (2006.01)
  *B29C 65/08* (2006.01)
  *B29L 31/00* (2006.01)

(52) U.S. Cl.
  CPC .......... *A61B 18/1477* (2013.01); *B29C 65/08* (2013.01); *B29C 65/48* (2013.01); *A61B 2017/00526* (2013.01); *A61B 2018/00178* (2013.01); *A61B 2018/00345* (2013.01); *A61B 2018/00577* (2013.01); *A61B 2018/00702* (2013.01); *A61B 2018/00922* (2013.01); *A61B 2018/00946* (2013.01); *A61B 2018/00958* (2013.01); *A61B 2018/1412* (2013.01); *B29L 2031/7546* (2013.01); *H01H 23/06* (2013.01); *H01H 2205/032* (2013.01); *H01H 2300/014* (2013.01)

(56) References Cited

U.S. PATENT DOCUMENTS

| | | | |
|---|---|---|---|
| 4,625,723 A | 12/1986 | Altnether et al. | |
| D301,739 S | 6/1989 | Turner et al. | |
| D330,253 S | 10/1992 | Burek | |
| 5,376,089 A | 12/1994 | Smith | |
| 5,453,087 A * | 9/1995 | Malinowski | A61F 9/00745 604/22 |
| D370,731 S | 6/1996 | Corace et al. | |
| D384,148 S | 9/1997 | Monson | |
| D393,067 S | 3/1998 | Geary et al. | |
| D402,030 S | 12/1998 | Roberts et al. | |
| D402,031 S | 12/1998 | Roberts et al. | |
| D433,752 S | 11/2000 | Saravia | |
| D441,077 S | 4/2001 | Garito et al. | |
| D453,222 S | 1/2002 | Garito et al. | |
| D453,833 S | 2/2002 | Hess | |
| D457,955 S | 5/2002 | Bilitz | |
| 3,558,383 A1 | 5/2003 | Cunningham et al. | |
| D493,530 S | 7/2004 | Reschke | |
| D493,888 S | 8/2004 | Reschke | |
| D494,270 S | 8/2004 | Reschke | |
| D495,051 S | 8/2004 | Reschke | |
| D495,052 S | 8/2004 | Reschke | |
| D515,412 S | 2/2006 | Waaler et al. | |
| D521,641 S | 5/2006 | Reschke et al. | |
| D535,396 S | 1/2007 | Reschke et al. | |
| 8,022,327 B2 | 9/2011 | Blomeyer | |
| 2002/0046938 A1 * | 4/2002 | Donofrio | H01H 9/04 200/302.1 |

FOREIGN PATENT DOCUMENTS

| | | |
|---|---|---|
| DE | 3045996 A1 | 7/1982 |
| DE | 19503702 A1 | 8/1996 |
| EP | 0181733 A1 | 5/1986 |
| FR | 2 235 669 A1 | 1/1975 |
| FR | 2798579 A1 | 3/2001 |
| JP | 55000243 A | 1/1980 |
| JP | 63082710 A | 4/1988 |
| JP | 07-143993 | 6/1995 |
| WO | 2004/045436 A1 | 6/2004 |
| WO | 2012155922 A2 | 11/2012 |
| WO | 201315830 A1 | 1/2013 |

OTHER PUBLICATIONS

Australian Examination Report dated Jul. 22, 2016, issued in Australian Application No. 2015230713.
European Search Report dated Mar. 3, 2016, issued in European Application No. 15186319.
Canadian Office Action dated Sep. 14, 2016, issued in Canadian Application No. 2,905,130.
Li et al., "Interactive Catheter Shape Modeling in Interventional Radiology Simulation" 2001, Springer, Berlin/Heidelberg vol. 2208, pp. 457-464.
Zucker, Karl, "Surgical Laparoscopy" Lippincott Williams & Wilkins, Ed. 2, 2001 2pp.
U.S. Appl. No. 14/857,913, filed Sep. 18, 2015, inventor: Stoddard et al.
European Office Action dated Jan. 2, 2019, issued in EP Appln. No. 15 186 319.
Australian Examination Report dated Feb. 1, 2017, issued in Australian Application No. 2015230713.

* cited by examiner

INGRESS PROTECTION FOR ELECTROSURGICAL PENCIL SWITCH

CROSS-REFERENCE TO RELATED APPLICATIONS

This application claims the benefit of, and priority to, U.S. Provisional Patent Application Nos. 62/053,981 and 62/053,992, both of which were filed on Sep. 23, 2014. This application is related to U.S. patent application Ser. No. 14/857,913, filed on Sep. 18, 2015, now U.S. Pat. No. 9,986,984. The entire contents of each of the above applications are hereby incorporated herein by reference.

BACKGROUND

1. Technical Field

The present disclosure relates to medical devices and methods of manufacturing the same. Specifically, to present disclosure relates fluid ingress protection in a surgical instrument and methods for assembling the same.

2. Discussion of Related Art

Electrosurgical medical devices have become widely used by surgeons. Electrosurgical medical devices may include a hand-held instrument, e.g., pencil, which transfers radio-frequency (RF) electrical energy to a tissue site from a suitable electrosurgical generator. The electrical current may be returned to the source via a return electrode pad positioned under a patient, or a smaller return electrode positioned in bodily contact, with or immediately adjacent to, the surgical site. The waveforms which result from the RF electrical current may be used to produce a variety of effects, depending on the power applied, and the frequency used. These effects include surgical cutting, coagulation, cauterization, or sealing.

As electrosurgical pencils are, even when assembled by humans, relatively small and simple devices, and used by medical professionals under circumstances which may benefit from a "disposable" tool, electrosurgical pencils have become less expensive to produce. However, like most manufactured items, and all medical tools (especially inexpensive medical tools), the cost of manufacture, and the distribution of electrosurgical pencils, along with the necessity to repurchase such "disposable" tools as they are discarded, adds greatly to their overall cost to the surgical profession and, ultimately, to their patients and health care costs. What is needed, then, is an even less resource intensive method of manufacturing electrosurgical pencils. The savings in resources may be achieved at the stage where the electrosurgical pencil switch circuitry is loaded into the molded insulative holding and positioning body of the electrosurgical pencil hand piece. Further savings may be achieved if a very low cost hand piece, which may be discarded after use, is matched with high quality electrical conductors (leading from the hand piece back to the generator), which may be retained and reused.

SUMMARY

In an aspect of the present disclosure, a surgical instrument includes a switch base, a power bus coupled to the switch base, an electrical lead coupled to the power bus, an actuator operatively engaged with the power bus, a membrane, and a housing. The switch base has top, bottom, and side surfaces. The membrane is disposed over at least the top surface of the switch base and over the power bus sealing the top surface of the switch base. The housing defines a proximal opening, and a switch base cavity between the proximal and distal ends. The housing includes a plurality of bulkheads forming a plurality of fluid impermeable seals disposed adjacent to at least one of the proximal or distal ends. The fluid impermeable seals are configured to deter fluid from penetrating a proximal portion of the switch base cavity within which the electrical lead is coupled to the power bus.

In aspects, the plurality of bulkheads includes upper bulkheads that extend from the housing. Each of the upper bulkheads may engage the membrane to form one of the plurality of fluid impermeable seals. The upper bulkheads may engage the membrane to form a secondary fluid impermeable seal between the membrane and a portion of the switch base cavity.

In some aspects, the membrane is disposed over the top surface and a portion of each of the side surfaces of the switch base. The membrane may be disposed entirely over each of the side surfaces and portions of the membrane may be disposed over portions of the bottom surface of the switch base.

In certain aspects, the membrane and the plurality of bulkheads prevent a fluid from contacting the switch base.

In particular aspects, the surgical instrument includes a cable enclosing at least one electrical lead and passing through at least one of the plurality of bulkheads. The cable may be mechanically coupled to the switch base. The cable may pass through at least one of the plurality of bulkheads positioned adjacent a proximal end of the switch base which forms one of the plurality of fluid impermeable seals with the cable. The plurality of bulkheads may include a proximal opening bulkhead positioned adjacent the proximal end of the switch base which forms one of the plurality of fluid impermeable seals with the cable.

In some aspects, the power bus includes an electrode connector extending proximally therefrom. The electrode connector defining an electrode opening that is configured to receive an electrode. The housing may include an electrode connector bulkhead disposed between the distal opening and the switch base that forms a fluid impermeable seal with the electrode connector.

In some aspects, the housing includes distal upper and lower bulkheads that form a fluid impermeable seal. The distal upper and lower bulkheads may form a fluid impermeable seal with the switch base.

In aspects, the housing includes a first housing portion and a second housing portion that are joined along mating surfaces. The mating surfaces may be substantially parallel to a longitudinal axis of the housing. The first housing portion may include a first half of at least one of the plurality of bulkheads and the second housing portion may include a second half of the at least one of the plurality of bulkheads.

In some aspects, the housing defines the actuator opening through an outer surface thereof. The actuator opening may be in communication with the switch base cavity. The actuator may be disposed within the actuator opening.

In another aspect of the present disclosure a surgical instrument includes a switch base, a power bus coupled to the switch base, a membrane, and a housing. The switch base has top, bottom, and side surfaces. The membrane is disposed over at least the top surface of the switch base and over the power bus to seal the top surface of the switch base. The housing defines a proximal opening, a distal opening, an actuator opening, and a switch base cavity including upper and lower portions. The housing includes a plurality of bulkheads that form a plurality of fluid impermeable seals that are disposed adjacent to at least one of the proximal, distal, or actuator openings. The fluid impermeable seals are configured to deter fluid from penetrating the switch base cavity.

In some aspects, the plurality of bulkheads includes upper bulkheads extending form the housing adjacent the actuator opening. Each of the upper bulkheads may engage the membrane to form one of the plurality of fluid impermeable seals.

In certain aspects, the membrane is disposed over the top surface and a portion of each of the side surfaces of the switch base.

In particular aspects, the surgical instrument includes a cable enclosing an electrical lead. The cable may pass through one of the plurality of bulkheads and extend through the proximal opening of the housing. The cable may pass through one of the plurality of bulkheads positioned adjacent a proximal end of the switch base which forms one of the plurality of fluid impermeable seals with the cable. The plurality of bulkheads includes a proximal opening bulkhead that is positioned adjacent the proximal opening and forms one of the plurality of fluid impermeable seals with the cable. The plurality of bulkheads may include a distal lower bulkhead and an electrode connector bulkhead that is disposed between the distal opening and the distal lower bulkhead. The distal lower bulkhead and the electrode connector bulkhead form one of the plurality of fluid impermeable seals with an electrode connector that extends proximally from the power bus.

In yet another aspect of the present disclosure, a method of assembling a surgical instrument includes coupling a power bus to a switch base that has a top, a bottom, and side surfaces; adhering a membrane to the top surface of the switch base over the power bus to form a switch base assembly; positioning the switch base assembly within a first portion of a switch base cavity defined by a lower housing portion; and joining the lower housing portion with an upper housing portion. The upper housing portion defines a second portion of the switch base cavity and the switch base is disposed within the first portion of the switch base cavity. Joining the upper and lower housing portions together prevents fluid from penetrating a proximal portion of the switch base cavity within which an electrical lead is coupled to the power bus.

In aspects, joining the lower housing portion with the upper housing portion includes engaging portions of the membrane adhered to each of the side surfaces of the switch base with walls of the first and second portions of the switch base cavity to form a fluid impermeable seal. Joining the lower housing portion with the upper housing portion may include forming proximal and distal lower bulkheads that together define the switch base cavity therebetween. Each of the proximal and distal lower bulkheads may engage and form a fluid impermeable seal with the switch base. Joining the lower housing portion with the upper housing portion may include applying adhesive, sonic welding, or laser welding.

In some aspects, the method includes positioning an actuator within an actuator opening that is defined by the second housing portion. The actuator opening may be in communication with the switch base cavity. The method may include electrically coupling a cable to the power bus.

In certain aspects, joining the lower housing portion with the upper housing portion includes engaging the membrane with upper bulkheads that extend from the upper housing portion towards the lower housing portion to form a fluid impermeable seal with the membrane. Engaging the membrane with the upper bulkheads may include compressing the membrane against the switch base.

In still yet another aspect of the present disclosure, a method of assembly a surgical instrument includes coupling a power bus to a switch base that has a top, a bottom, and side surfaces; adhering a membrane to the top surface of the switch base over the power bus to form a switch base assembly; positioning the switch base assembly within a first portion of a switch base cavity defined by a lower housing partition; and joining the lower housing portion with an upper housing portion that defines a second portion of the switch base cavity. The switch base is disposed within the first portion of the switch base cavity such that fluid is prevented from penetrating the first portion of the switch base cavity.

In some aspects, joining the lower housing portion with the upper housing portion includes engaging portions of the membrane adhered to side surfaces of the switch base with walls of the first and second portions of the switch base cavity to form a seal. Joining the lower housing portion with the upper housing portion may include forming proximal and distal switch base bulkheads that define the switch base cavity therebetween. The proximal and distal switch base bulkheads may engage and form a seal with the switch base. Joining the lower housing portion with the upper housing portion may include applying adhesive, sonic welding, or laser welding. Joining the lower housing portion with the upper housing portion may include engaging the membrane with switch protrusions that extend from the upper housing portion towards the lower housing portion to form a seal with the membrane. Engaging the membrane with the switch protrusions may include comprising the membrane against the switch base.

In certain aspects, the method may include positioning a switch within a switch opening that is defined by the upper housing portion. The switch opening may be in communication with the switch base cavity.

In particular aspects, the method may include electrically coupling a power cable to the power bus.

The assembly of the presently disclose electrosurgical pencil reduces the cost of manufacture by eliminating hand labor during the assembly of the electrosurgical pencil. The design of electrosurgical pencil allows this by forming a seal between the exposed switch and other electrical components, which allows for complete machine assembly. This saves significant manufacturing costs, which results in the saving unnecessary costs for the surgeon and savings to the patient.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
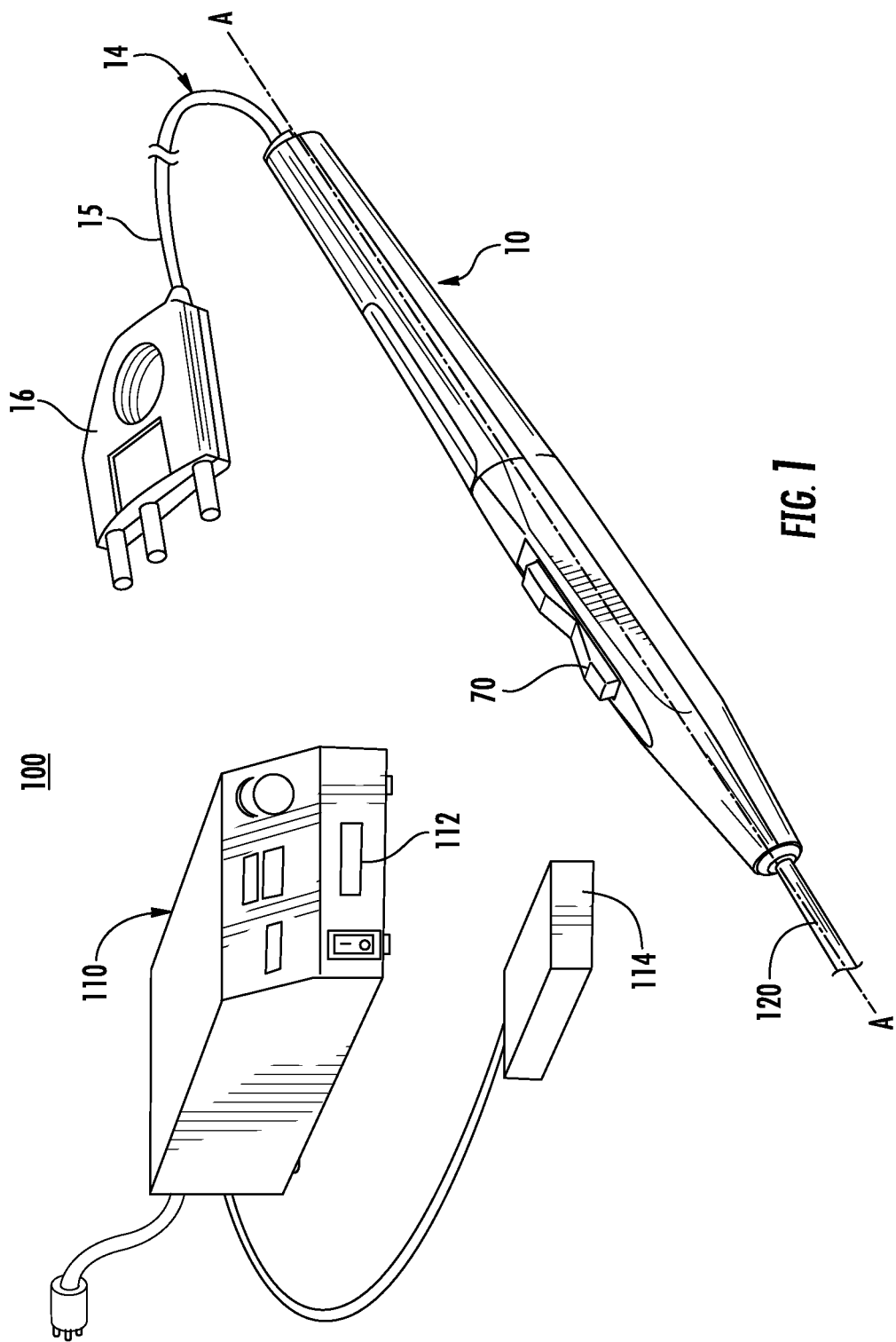
FIG. 1 is a perspective view of an exemplary electrosurgical system including an electrosurgical pencil in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure provides for electrosurgical devices (e.g., pencils) and methods for assembling the same. The presently disclosed electrosurgical devices are configured to be assembled in automated manner or with minimal manual labor while sealing the electrical components within the housing and preventing fluid and other contaminants from contacting into the electrical components. The electrosurgical device according to the present disclosure includes a membrane disposed over electrical components of the device, (e.g., switch base and power bus), which in turn is disposed within a housing including a plurality of bulkheads. The combination of the membrane and the bulkheads provide for a fluid impermeable seal for the electrical components of the device. As used herein, the term "fluid impermeable" includes fluid resistant or fluid proof and denotes making the electrical components impervious to fluids and any other contaminants.

Referring now to FIG. 1, an exemplary embodiment of an electrosurgical system 100 in accordance with the present disclosure is shown and includes an electrosurgical pencil 10, an electrosurgical generator 110, and an electrode 120. The generator 110 is configured to provide electrosurgical energy to the pencil 10 allowing the pencil 10 to coagulate, ablate, or otherwise treat tissue. The generator 110 includes a receptacle 112 or a cable (not shown) to connect to the pencil 10 as detailed below. In embodiments, the pencil 10 is a monopolar pencil includes an active electrode 120 and the generator 110 includes a return electrode or pad 114 that is placed in contact with a patient during use of the pencil 10. It is also contemplated that the pencil 10 may be a bipolar pencil including a return electrode.

Figure 2:
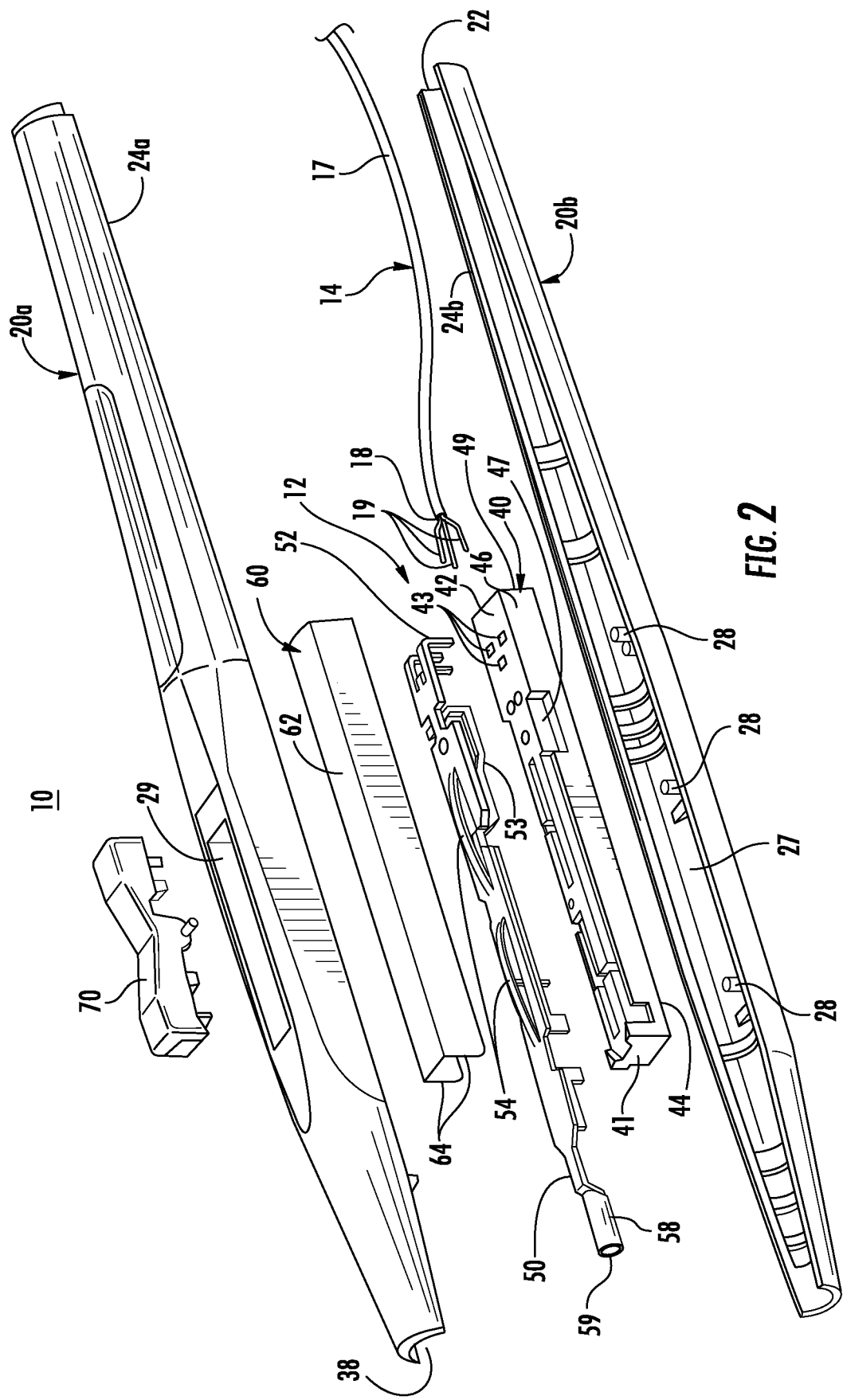
FIG. 2 is an exploded view showing the components of the electrosurgical pencil of FIG. 1 in accordance with the present disclosure.
Figure 3:
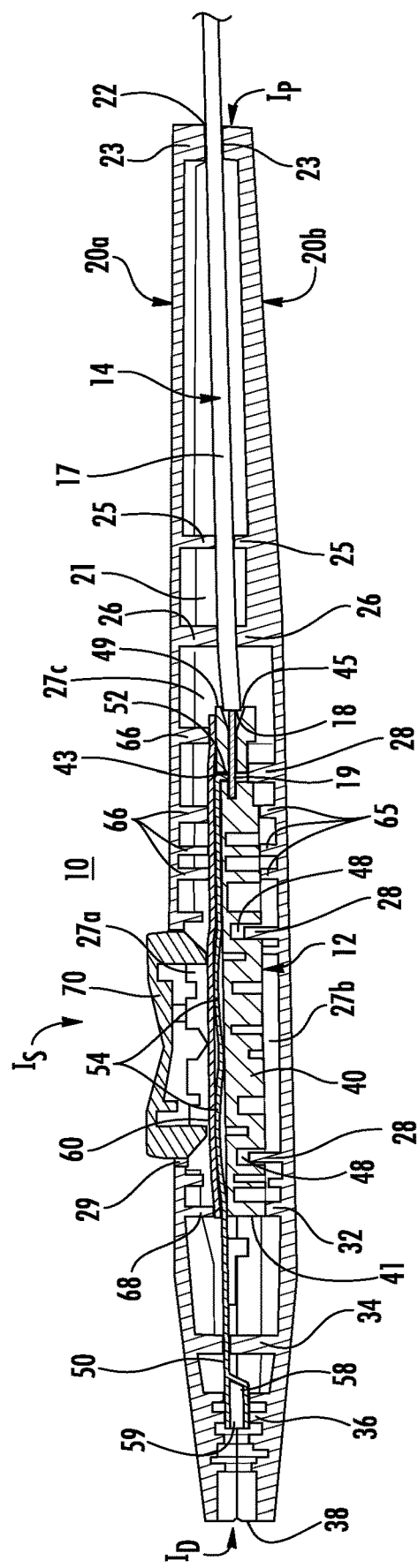
FIG. 3 is a side cross-sectional view taken along the longitudinal axis of the electrosurgical pencil of FIG. 1 in accordance with the present disclosure.

Referring to FIGS. 2 and 3, the pencil 10 includes a first or upper housing portion 20a and a second or lower housing portion 20b that are coupled together to form a housing 20 (FIG. 1), which defines a longitudinal axis A-A. The housing portions 20a, 20b are coupled together along mating surfaces 24a, 24b that are substantially parallel to the longitudinal axis A-A to form a seal along the mating surfaces 24a, 24b. The housing portions 20a, 20b may be coupled together by applying adhesive, sonic welding, laser welding, or any other suitable methods.

The housing portions 20a, 20b together define a proximal opening 22, a distal opening 38, and a tortuous path 21 therebetween. The tortuous path 21 includes a proximal switch base bulkhead 26 and a distal lower bulkhead 32 defining a switch base cavity 27 therebetween.

With continued reference to FIGS. 2 and 3, the pencil 10 includes a switch base assembly 12 positioned within the switch base cavity 27 and a power cable 14 passing through the proximal opening 22, which is coupled to the switch base assembly 12. The switch base assembly 12 includes a switch base 40, a power bus 50, and a flexible membrane 60.

The switch base 40 may be constructed of a nonconductive material (e.g., thermoplastics, ceramics, and dielectric polymers). The switch base 40 has a distal end surface 41, a top surface 42, a bottom surface 44, side surfaces 46, and a proximal end surface 49. The top surface 42 defines bus openings 43 (FIG. 2) for receiving portions of the power bus 50. The proximal end surface 49 defines a connector opening 45 adjacent a proximal end of the switch base 40. The side surfaces 46 may define cutouts 47 adjacent the top surface 42.

The power bus 50 is coupled to the top surface 42 of the switch base 40 and is constructed of a conductive material (e.g., copper, silver, gold, stainless steel, various alloys and combinations thereof). The power bus 50 may be stamped from a single piece of conductive material. The power bus 50 includes prongs 52, switch contacts 54, and an electrode contact 58. The power bus 50 may include side protrusions 53 extending into the cutouts 47 of the switch base 40. The side protrusions 53 align the power bus 50 with the switch base 40 and may secure the power bus 50 to the switch base 40. In embodiments, the side protrusions 53 capture portions of the switch base 40 therebetween to secure the power bus 50 to the switch base 40.

An electrode 120 (FIG. 1) is coupled to the electrode contact 58 of the power bus 50. The electrode contact may define an electrode opening 59 that frictionally receives the electrode 120 (FIG. 1). The electrode contact 58 extends through the distal lower bulkhead 32 from the switch base 40. The tortuous path 21 includes the electrode bulkhead 34, such that the electrode contact 58 may pass through and form a fluid impermeable seal with the electrode bulkhead 34.

Each of the prongs 52 extends into a respective bus opening 43 to electrically engage a respective lead 19 of cable 14 to create an insulated displacement connection with the respective lead 19. Each of the switch contacts 54 has a non-activated position and an activation position. In the non-activated position, a conductive path is broken and in the activated position, a conductive path is formed between the corresponding prong 52 and the electrode contact 58. When a conductive path is formed, energy is permitted to pass from the generator 110 to the electrode contact 58.

With reference to FIGS. 1-3, the power cable 14 includes a proximal end 15 (FIG. 1), a distal end 18, and a sheath 17 therebetween. The proximal end 15 includes a plug 16 (FIG. 1) that releasably couples to the generator 110 (e.g., the plug 16 is received within the receptacle 112 of the generator). The distal end 18 includes connectors or leads 19 that insert into the connector opening 45 (FIG. 3) of the switch base 40 such that each of the leads 19 is positioned within one of the bus openings 43.

The bottom surface 44 of the switch base 40 may define keyed openings 48 (FIG. 3) and the housing portion 20b may include keys 28 that are received within the keyed openings 48 to longitudinally position and fix the switch base 40 within the switch base cavity 27. The keys 28 may be received within the keyed openings 48 to seal a portion of the switch base 40 (e.g., the proximal most keys 28 may seal the lower end of the bus openings 43. It is contemplated that the keys 28 may be slightly larger than the keyed openings 48 such that when the keys 28 are received within the keyed openings 48 the keys 28 frictionally secure the switch base 40 within the switch base cavity 27. In addition, the keys 28 also prevent fluid from entering the openings 43 and contacting the prongs 52 and/or leads 19.

The membrane 60 also forms a fluid impermeable seal with the switch base assembly 12 to prevent fluid from contacting the prongs 52, the switch contacts 54, or other electrical connections of the switch base assembly 12. The membrane 60 may be constructed of a flexible non-conductive material applied with adhesive on the side facing the switch base 40, which allows the actuator 70 to engage the switch contacts 54. Suitable non-conductive materials include, but are not limited to, polymeric materials, such as polyester films or ionically cross-linked thermoplastics based upon ethylene copolymerised with carboxyl groups and a metal ions. It is contemplated that the flexible membrane 60 is a laminate of materials including polyester for strength, a resin layer for toughness, and an adhesive layer. It will be appreciated that the flexible membrane may be resilient, yet flexible to allow for deflection of the switch contacts 54 without reducing the tactile feel of the switch contacts 54.

The membrane 60 includes a top portion 62 that is disposed over the top surface 42 of the switch base 40 and the power bus 50. The membrane 60 may be adhered using adhesive and/or formed as a film over the switch base 40 and the power bus 50 and allowed to dry and adhere thereto. The top portion 62 may be adhered to the top surface 42 of the switch base 40 and/or the power bus 50. The membrane 60 includes side portions 64 that extend from the top portion 62 towards the bottom surface 44 of the switch base 40 to form a fluid impermeable seal with the side surfaces 46 of the switch base 40. The side portions 64 may be adhered to the side surfaces 46 of the switch base 40 and/or the power bus 50. In embodiments, the membrane 60 may include bottom portions (not shown) that extend from the side portions 64 towards one another and form a fluid impermeable seal with the bottom surface 44 of the switch base 40. The bottom portions (not shown) may be adhered to the bottom surface 44 of the switch base 40.

With reference to FIG. 3, the housing portion 20a defines a switch opening 29 in communication with an upper portion 27a of the switch base cavity 27. An actuator 70 is disposed within the switch opening 29. The actuator 70 may be a rocker switch that rocks (e.g., pivots) within the switch opening 29 to activate switch contacts 54 as described above. Alternatively, the actuator 70 may be one or more push buttons (not shown) positioned within the switch opening 29. It will be appreciated that fluid may ingress through the switch opening 29, switch ingress $I_S$ (FIG. 3), into the upper portion 27a of the switch base cavity 27.

With reference to FIG. 3, the pencil 10 includes features (e.g., membrane 60 and proximal and distal upper bulkheads 66, 68) to prevent the fluid ingressing through the switch opening 29 (e.g., switch fluid ingress $I_S$), through the proximal opening 22 (proximal fluid ingress $I_P$), and through the distal opening 38 (e.g., distal fluid ingress $I_D$) from contacting electrical components within the switch base cavity 27. The tortuous path 21 includes a plurality of bulkheads (e.g., bulkheads 25, 32, 34, 65, 66, etc.) that limit fluid ingress into the switch base cavity 27, such that in instances in which any fluid that penetrates through the bulkheads is retained in compartments defined therebetween in the tortuous path 21.

In particular, when the switch base assembly 12 is disposed within the switch base cavity 27 of the tortuous path 21, portions of the tortuous path 21 engage the membrane 60 to form a fluid impermeable seal with the membrane 60 to prevent fluid from contacting the prongs 52, the switch contacts 54, or other electrical connections of the switch base assembly 12. With particular reference to FIG. 3, the first housing portion 20a includes proximal and distal upper bulkheads 66, 68 that extend downward towards the second housing portion 20b. The proximal upper bulkhead 66 are positioned adjacent a proximal end of the switch opening 29 and the distal upper bulkhead 68 are positioned adjacent a distal end of the switch opening 29. The proximal and distal upper bulkheads 66, 68 engage the membrane 60 to form a fluid impermeable seal with the membrane 60 to prevent fluid from contacting the switch contacts 54 or electrical connections of the switch base assembly 12. Additionally, the proximal and distal upper bulkheads 66, 68 compress the membrane 60 against the switch base 40 and/or the power bus 50 to form a fluid impermeable seal. The second housing portion 20b includes a plurality of proximal lower bulkheads 65, which extend upward toward the first housing portion 20a. The proximal lower bulkheads 65 engage the bottom surface 44 of the switch base 40 to prevent fluid from contacting the switch contacts 54 or electrical connections of the switch base assembly 12.

First and second housing portions 20a and 20b also include a switch base bulk head 26, a cable bulkhead 25, and a proximal opening bulkhead 23 to prevent proximal fluid ingress $I_P$ from reaching proximal portion 27c of the switch base cavity 27. More specifically, the sheath 17 of the cable 14 forms a fluid impermeable seal with each of the proximal switch base bulkhead 26, cable bulkhead 25, and the proximal opening bulkhead 23. The proximal opening bulkhead 23 is positioned adjacent the proximal opening 22 to prevent proximal fluid ingress $I_P$ through the proximal opening 22 from contacting electrical components within the switch base cavity 27. The power cable bulk head 25 is positioned between the proximal opening 22 and the proximal switch base bulk head 26 to further prevent proximal fluid ingress $I_P$ through the proximal opening 22 from contacting electrical components within the switch base cavity 27.

In embodiments, the tortuous path 21 also includes a distal opening bulkhead 36 positioned adjacent the distal opening 38 to further prevent distal fluid ingress $I_D$ (FIG. 3) through the distal opening 38 from contacting electrical components within the switch base cavity 27. In certain embodiments, the tortuous path 21 includes an electrode bulkhead 34 positioned between the distal lower bulkhead 32 and the distal opening 38 to further prevent distal fluid ingress $I_D$ (FIG. 3) through the distal opening 38 from contacting electrical components within the switch base cavity 27. In further embodiments, the tortuous path 21 also includes a distal lower bulkhead 32, which seals the switch base cavity 27 to prevent distal fluid ingress $I_D$ (FIG. 3) through the distal opening 38 from contacting electrical components within the switch base cavity 27.

Referring to FIGS. 2 and 3, the assembly of the pencil 10 is detailed in accordance with the present disclosure. The switch base assembly 12 is assembled by coupling the power cable 14 to the switch base 40, coupling the power bus 50 to the switch base 40, and adhering the membrane 60 to the switch base 40. The leads 19 of the power cable 14 are inserted into the connector opening 45 in the proximal end surface 49 of the switch base 40 to couple the power cable 14 to the switch base 40. Each of the prongs 52 is electrically coupled to a respective one of the leads 19 when the prongs 52 are inserted into the bus openings 43.

To couple the power bus 50 to the switch base 40, the prongs 52 are inserted into the bus openings 43 defined by the top surface 42 such that each of the prongs 52 is in electrical communication with one of the leads 19 and the electrode contact 58 extends distally from the top surface 42 of the switch base 40. In embodiments where the power bus 50 includes side protrusions 53, the side protrusions 53 are received within the cutouts 47 in the side surfaces 46 of the switch base 40. The side protrusions 53 may assist in aligning and positioning the power bus 50 relative to the switch base. The side protrusions 53 may be portions of the switch contacts 54 that are disconnected from the power bus 50 adjacent the bus openings 43 after the power bus 50 is installed and the electrical connects are made between the leads 19 and the prongs 52.

With the power bus 50 coupled to the top surface 42 of the switch base 40, the membrane 60 is adhered to the switch base 40 to seal the top surface 42 of the switch base 40 and the power bus 50. The membrane 60 may be adhered to the top surface 42 of the switch base 40 over the power bus 50. Additionally or alternatively, the membrane 60 may extend from the top surface 42 over a portion of the side surfaces 46 and may be adhered to the side surfaces 46. In some embodiments, the membrane 60 may extend over each side surface 46 and portions of the membrane 60 may extend over a portion of the bottom surface 44 and may be adhered to the bottom surface 44. Additionally, the membrane 60 may extend over portions of the power cable 14.

With the switch base assembly 12 assembled, the switch base assembly 12 is secured within the switch base cavity 27. The switch base assembly 12 is aligned with the second housing portion 20b such that the switch base 40 is positioned in the lower portion 27b of the switch base cavity 27 defined by the second housing portion 20b. The proximal end of the switch base 40 may engage the proximal switch base bulkhead 26 or the distal end of the switch base 40 may engage the distal lower bulkhead 32. Additionally or alternatively, each of the keys 28 of the second housing portion 20b engage a respective keyed opening 48 defined in the bottom surface 44 of the switch base 40 to align the switch base 40 with the second housing portion 20b. The sheath 17 of the power cable 14 is positioned in the tortuous path 21 passing through the proximal opening 22. The sheath 17 may pass through and form a fluid impermeable seal with each of the proximal switch base bulk head 26, the cable bulkhead 25, and the proximal opening bulkhead 23. The electrode connector 58 may pass through and form a fluid impermeable seal with each of the distal lower bulkhead 32 and the electrode bulkhead 34.

The first housing portion 20a is positioned over the second housing portion 20b and the switch base assembly 12 such that the switch base assembly 12 is aligned with the upper portion 27a of the switch base cavity 27 defined by the first housing portion 20a. The actuator 70 is positioned between the first housing portion 20a and the switch base assembly 12. The actuator 70 is pressed into the first housing portion 20a such that the actuator 70 is pivotally coupled to the first housing portion 20a. The actuator 70 may be pressed into the first housing portion 20a before the first housing portion 20a is positioned over the first housing portion 20a and the switch base assembly 12.

Next, the first housing portion 20a is pressed over the switch base assembly 12. The proximal and distal upper bulkheads 66, 68 extending from the first housing portion 20a engage the membrane to form a fluid impermeable seal with the membrane 60 to prevent fluid ingressing into the upper portion 27a of the switch base cavity 27 through the switch opening 29 from contacting the switch contacts 54 or other electrical connections of the switch base assembly 12. Additionally, the proximal and distal upper bulkhead 66, 68 may compress the membrane 60 against the switch base 40 and/or the power bus 50. The first housing portion 20a is pressed over the switch base assembly 12 until the mating surfaces 24a, 24b of each of the first and second housing portions 20a, 20b in contact with one another. The first and second housing portions 20a, 20b are then coupled together in a sealing relationship by applying adhesive, sonic welding, laser welding, or any other suitable methods.

With the first and second housing portions 20a, 20b coupled together, fluid is prevented from contacting portions of the switch contacts 24 and the electrical connections of the switch base assembly 12. The lower portion 27b of the switch base cavity 27 is sealed in a fluid proof manner by at least the membrane 60, the proximal switch base bulkhead 26, the distal lower bulkhead 32, and the second housing portion 20b.

It is contemplated that the assembly of the pencil 10 as detailed herein may be completely automated (i.e., without the need for hand labor during the assembly).

It is contemplated that fluid may enter the pencil 10 through the switch opening 29 into the upper portion 27a of the switch base cavity 27 defined by the first housing portion 20a, the proximal opening 22, and the distal opening 38. As such, the membrane 60 is positioned to prevent fluid that enters the pencil 10 through the switch opening 29 from penetrating the lower portion 27b of the switch base cavity 27 and contacting the switch contacts 54 and other electrical connections of the switch base assembly 12. The proximal switch base bulkhead 26 prevents fluid that enters the pencil through the proximal opening 22 from penetrating the switch base cavity 27. In addition, the proximal opening bulkhead 23 or the cable bulkhead 25 may prevent fluid that enters the pencil 10 through the proximal opening 22 from penetrating the switch base cavity 27. The distal lower bulkhead 32 prevents fluid that enters the pencil 10 through the distal opening 38 from penetrating the switch base cavity 27. In addition, the electrode bulkhead 34 and the distal opening bulkhead 36 may prevent fluid that enters the pencil 10 through the distal opening 38 from penetrating the switch base cavity 27.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:
1. A surgical instrument comprising:
a switch base having a top surface, a bottom surface, and side surfaces;
a power bus coupled to the switch base;
at least one electrical lead coupled to the power bus;
a membrane disposed over at least the top surface of the switch base and over the power bus sealing the top surface of the switch base; and
a housing defining a proximal end, a distal end, and a switch base cavity between the proximal and distal ends, the housing including a plurality of bulkheads forming a plurality of fluid impermeable seals within the housing and disposed adjacent to at least one of the proximal end or the distal end, a first bulkhead of the plurality of bulkheads forming a proximal fluid impermeable seal proximal of the switch base cavity configured to deter fluid from penetrating a proximal portion of the switch base cavity within which the at least one electrical lead is coupled to the power bus, wherein the plurality of bulkheads includes a proximal bulkhead extending from the housing and engaged to a portion of the membrane that is disposed over a proximal end portion of the switch base.

2. The surgical instrument of claim 1, wherein the membrane is disposed over the top surface and a portion of each of the side surfaces of the switch base.

3. The surgical instrument of claim 2, wherein the membrane is disposed entirely over each of the side surfaces and portions of the membrane are disposed over portions of the bottom surface of the switch base.

4. The surgical instrument of claim 1, wherein the membrane and the plurality of bulkheads prevent a fluid from contacting with the switch base.

5. The surgical instrument of claim 1 further comprising a cable enclosing at least one electrical lead, the cable passing through and engaged by the first bulkhead.

6. The surgical instrument of claim 5, wherein the plurality of bulkheads includes a proximal opening bulkhead positioned proximally of the first bulkhead and adjacent the proximal opening which forms one of the plurality of fluid impermeable seals with the cable.

7. The surgical instrument of claim 1, wherein the housing includes distal upper and lower bulkheads that form a distal fluid impermeable seal.

8. The surgical instrument of claim 7, wherein the distal upper and lower bulkheads form the distal fluid impermeable seal with the switch base.

9. The surgical instrument of claim 1, wherein the housing includes a first housing portion and a second housing portion, the first and second housing portions joined along mating surfaces that are parallel to a longitudinal axis of the housing.

10. The surgical instrument of claim 9, wherein the first housing portion includes a first half of at least one of the plurality of bulkheads and the second housing portion includes a second half of the at least one of the plurality of bulkheads.

11. The surgical instrument of claim 1 further comprising an actuator operatively engaged with the power bus, wherein the housing defines an actuator opening through an outer surface thereof, the actuator opening being in communication with the switch base cavity and the actuator being disposed within the actuator opening.

12. A surgical instrument comprising:
a switch base having a top surface, a bottom surface, and side surfaces;
a power bus coupled to the switch base;
a membrane disposed over at least the top surface of the switch base and over the power bus sealing the top surface of the switch base; and
a housing defining a proximal opening, a distal opening, an actuator opening, and a switch base cavity including an upper portion and a lower portion, the housing including a plurality of bulkheads forming a plurality of fluid impermeable seals within the housing and disposed adjacent to at least one of the proximal opening, the distal opening, or the actuator opening, the fluid impermeable seals configured to prevent fluid from penetrating the switch base cavity, wherein the plurality of bulkheads includes a proximal bulkhead extending from the housing and engaged to a portion of the membrane that is disposed over a proximal end portion of the switch base.

13. The surgical instrument of claim 12, wherein the plurality of bulkheads includes upper bulkheads extending from the housing between the actuator opening and the proximal bulkhead, each of the upper bulkheads engaging the membrane to form one of the plurality of fluid impermeable seals.

14. The surgical instrument of claim 12, wherein the membrane is disposed over the top surface and a portion of each of the side surfaces of the switch base.

15. The surgical instrument of claim 12, further comprising a cable enclosing at least one electrical lead, the cable extending through the proximal opening of the housing, wherein the cable passes through and is engaged by the proximal bulkhead.

16. The surgical instrument of claim 15, wherein the plurality of bulkheads includes a proximal opening bulkhead positioned proximally of the proximal bulkhead and adjacent the proximal opening which forms another of the plurality of fluid impermeable seals with the cable.

17. The surgical instrument of claim 16, wherein the plurality of bulkheads includes a distal lower bulkhead and an electrode connector bulkhead disposed between the distal opening and the distal lower bulkhead, each of the distal lower bulkhead and the electrode connector bulkhead form one of the plurality of fluid impermeable seals with an electrode connector extending proximally from the power bus.

* * * * *